US006638404B2

(12) United States Patent
Terashima et al.

(10) Patent No.: US 6,638,404 B2
(45) Date of Patent: Oct. 28, 2003

(54) ION SELECTIVE ELECTRODE

(75) Inventors: Masaaki Terashima, Saitama (JP); Osamu Seshimoto, Saitama (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 24 days.

(21) Appl. No.: 09/911,290

(22) Filed: Jul. 23, 2001

(65) Prior Publication Data

US 2002/0033335 A1 Mar. 21, 2002

(30) Foreign Application Priority Data

Jul. 21, 2000 (JP) .................................... 2000-220974

(51) Int. Cl.[7] ............................................ G01N 27/333
(52) U.S. Cl. ........................................ 204/416; 204/418
(58) Field of Search ................................ 204/416, 418, 204/419, 420

(56) References Cited

U.S. PATENT DOCUMENTS 4,502,938 A * 3/1985 Covington et al.
4,571,293 A * 2/1986 Seshimoto et al.
4,713,165 A * 12/1987 Conover et al.
4,789,435 A * 12/1988 Seshimoto et al.
4,871,441 A * 10/1989 Tsunekawa et al.
5,964,994 A * 10/1999 Craig et al.

* cited by examiner

Primary Examiner—T. Tung
(74) Attorney, Agent, or Firm—Reed Smith LLP

(57) ABSTRACT

In the manufacture of an ion selective electrode composed of a non-electroconductive support, a pair of electrodes each of which has a silver metal layer and a silver halide layer, an electrolytic material layer, an ion selective membrane, and a non-electroconductive sheet having a pair of openings for receiving a sample solution and a reference solution, respectively, and having thereon a bridge member for electrically connecting the sample solution received in one opening and the reference solution received in another opening, the ion selective membrane is advantageously divided into two separate portions, one of which is placed in a position above one electrode and another of which is placed in a position above another electrode.

2 Claims, 6 Drawing Sheets

ION SELECTIVE ELECTRODE

CROSS-REFERENCES TO RELATED APPLICATIONS

This application claims priority of Japanese Application No. 2000-220974 filed Jul. 21, 2000, the complete disclosure of which is hereby incorporated by reference.

FIELD OF THE INVENTION

This invention relates to an ion selective electrode favorably employable for analysis of ionic components in a whole blood sample or a serum sample.

BACKGROUND OF THE INVENTION

An ion selective electrode is widely employed for analyzing ionic components in a liquid sample such as a whole blood sample or a serum sample.

U.S. Pat. No. 4,571,293 (which corresponds to EP 0 160 997 B1) discloses an ion selective electrode which is illustrated in FIG. 6 of the drawings attached to this specification. In FIG. 6, the ion selective electrode comprises a non-electroconductive support 11, a pair of electrodes each of which comprises a silver metal layer 12a, 12b and a silver halide layer 13a, 13b, an electrolytic material layer 14, an ion selective membrane 15, and a non-electroconductive cover sheet 16 having a pair of openings 17a, 17b for receiving a sample solution and a reference solution, respectively, each opening being placed above each electrode unit, and having thereon an a bridge member 17 for electrically connecting the sample solution received in one opening and the reference solution received in another opening.

In industry, the ion selective electrode such as that illustrated in FIG. 6 is generally manufactured in a mass scale, by the steps of:

preparing a continuous longitudinal polymer sheet having thereon a composite film of a silver metal layer and a silver halide layer, and an electrolytic material layer, in order, in which the composite film is divided into two electrically insulated portions by a slit extending in a longitudinal direction thereof and further into plural electrically insulated units by slits extending in a direction traversing the longitudinal direction;

coating an ion selective membrane over the electrolytic material layer;

placing a non-electroconductive sheet having a pair of openings and a bridge member under the condition that each opening is placed on each spot of ion selective membrane; and separating the continuous longitudinal polymer sheet, the electrolytic layer, the ion selective membrane, and the non-electroconductive sheet along the slits extending in the traverse direction.

The above-described industrial method is advantageous for manufacturing a great number of ion selective electrodes in a mass scale.

U.S. Pat. No. 4,789,435 describes an ion selective electrode assembly comprising plural ion selective electrodes for analyzing plural ionic components such as $Na^+$, $K^+$, and $Cl^-$, simultaneously. In the assembly, one of plural ion selective electrodes has an ion selective membrane differing from that of other ion selective electrode in chemical composition.

The ion selective membrane comprises a combination of specifically selected materials, and the materials are very expensive.

SUMMARY OF THE INVENTION

It is an object of the present invention to provide an ion selective electrode having satisfactory analytical performance at a relatively low production cost.

The object of the invention also resides in providing a method of manufacturing ion selective electrodes having satisfactory analytical performance in a mass scale at a relatively low production cost.

The present invention resides in an ion selective electrode comprising, in order, a non-electroconductive support, a pair of electrodes each of which comprises a silver metal layer and a silver halide layer, an electrolytic material layer, an ion selective membrane, and a non-electroconductive sheet having a pair of openings for receiving a sample solution and a reference solution, respectively, each opening being placed above each electrode, and having thereon a bridge member for electrically connecting the sample solution received in one opening and the reference solution received in another opening, which is characterized in that the ion selective membrane is divided into two separate portions, one of which is placed in a position above one electrode and another of which is placed in a position above another electrode.

The ion selective electrode of the invention is preferably manufactured in a mass scale by the method comprising the steps of:

preparing a continuous longitudinal polymer sheet having thereon a composite film of a silver metal layer and a silver halide layer, and an electrolytic material layer, in order, in which the composite film is divided into two electrically insulated portions by a slit extending in a longitudinal direction thereof and further into plural electrically insulated units by slits extending in a direction traversing the longitudinal direction;

placing a spot of ion selective membrane on the electrolytic material layer in a position above each insulated composite film;

placing a non-electroconductive sheet having plural pair of openings and bridge members under the condition that each opening is placed on each spot of ion selective membrane; and dividing the continuous longitudinal polymer sheet, the electrolytic layer, and the non-electroconductive sheet along the slits extending in the traverse direction.

DETAILED DESCRIPTION OF THE INVENTION

The present invention is further described by referring to the figures illustrated in the attached drawings.

For manufacturing the ion selective electrodes in a mass scale, a continuous longitudinal polymer sheet having thereon a silver metal layer. The silver metal layer is generally placed on the polymer sheet by a deposition process. The polymer sheet generally is a polyethylene terephthalate sheet. On both side areas of the silver metal layer are coated with a polymer film for protecting the silver metal layer in the coated area from oxidization in the following chemical processing procedure. The polymer film can be produced from a film-forming resist resin solution.

Figure 1:
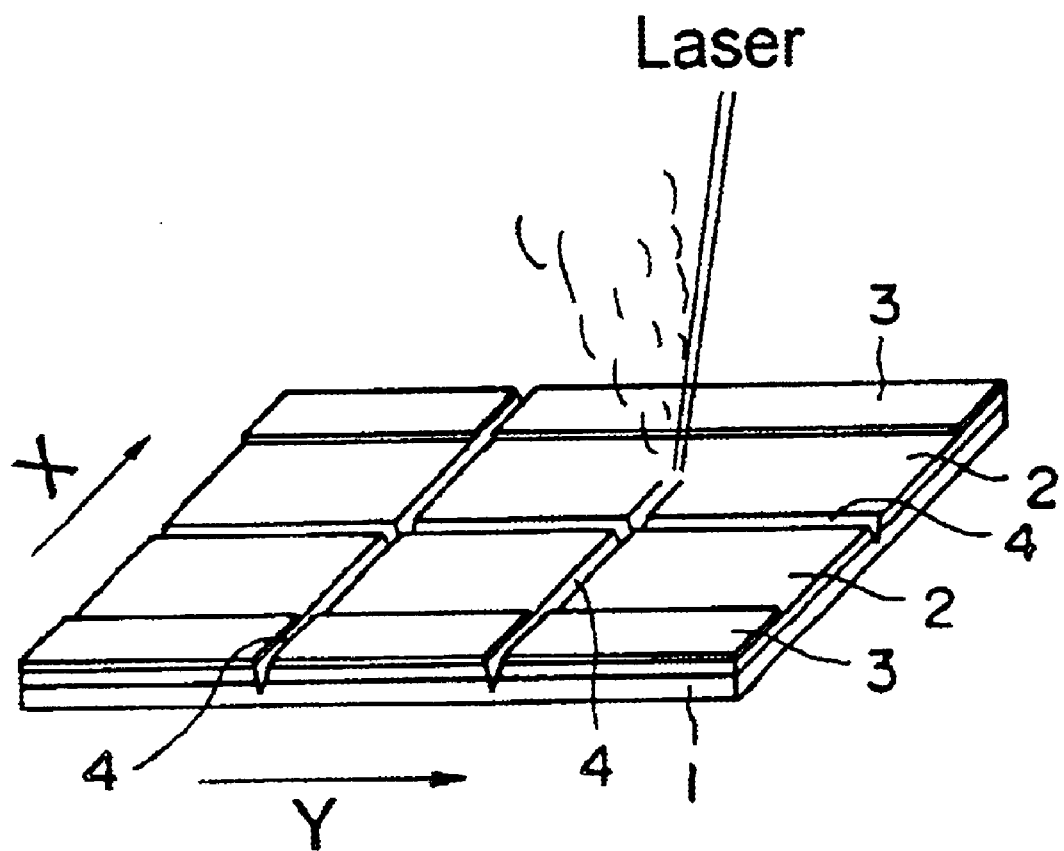
FIG. 1 illustrates an initial procedure (division of electrode layer into several electrode potions) for manufacturing ion selective electrodes according to the present invention.

In the next step, as is illustrated in FIG. 1, onto the continuous polymer sheet 1 having a silver metal layer 2 partly coated with a polymer film 3 are then provided several slits (or scratches) 4. Every slit 4 divides the silver metal layer 2 to portions which are electrically insulated from each other. One slit is provided to extend in the longitudinal direction (Y-direction), and other slits are provided to extend in directions (X-directions) traversing the Y-direction.

The slits in the X-direction are provided to separate ion selective electrode units In FIG. 1, three ion selective electrode units are produced. The slit in the Y-direction is provided to separate the electrode layer in one electrode unit to give two electrode portions, one of which is to potentiometrically detect a target ionic component in a sample solution, while another is to potentiometrically detect the same ionic component in a reference solution. The slits can be provided by applying a laser beam onto the surface of the silver metal layer, as is seen in FIG. 1. Otherwise, the slit can be formed by linearly scratching the surface of silver metal layer using a cutter.

The slits may be provided after a silver halide layer is formed on the silver metal layer. The details of the silver halide layer formation are described hereinbelow.

The polymer sheet having the silver metal layer and the polymer films coated on both side areas of the silver metal layer is then brought into contact with an oxidizing solution (e.g., dichromate solution or PDTA Fe(III) solution) for performing chemical oxidation-chlorination processing of the surface portion of the silver metal layer. Otherwise, a composition of silver halide particles and a binder are coated on the silver metal layer.

Thus, plural electrode layers each of which is composed of a silver metal layer and a silver halide layer coated over the silver metal layer are produced.

Figure 2:
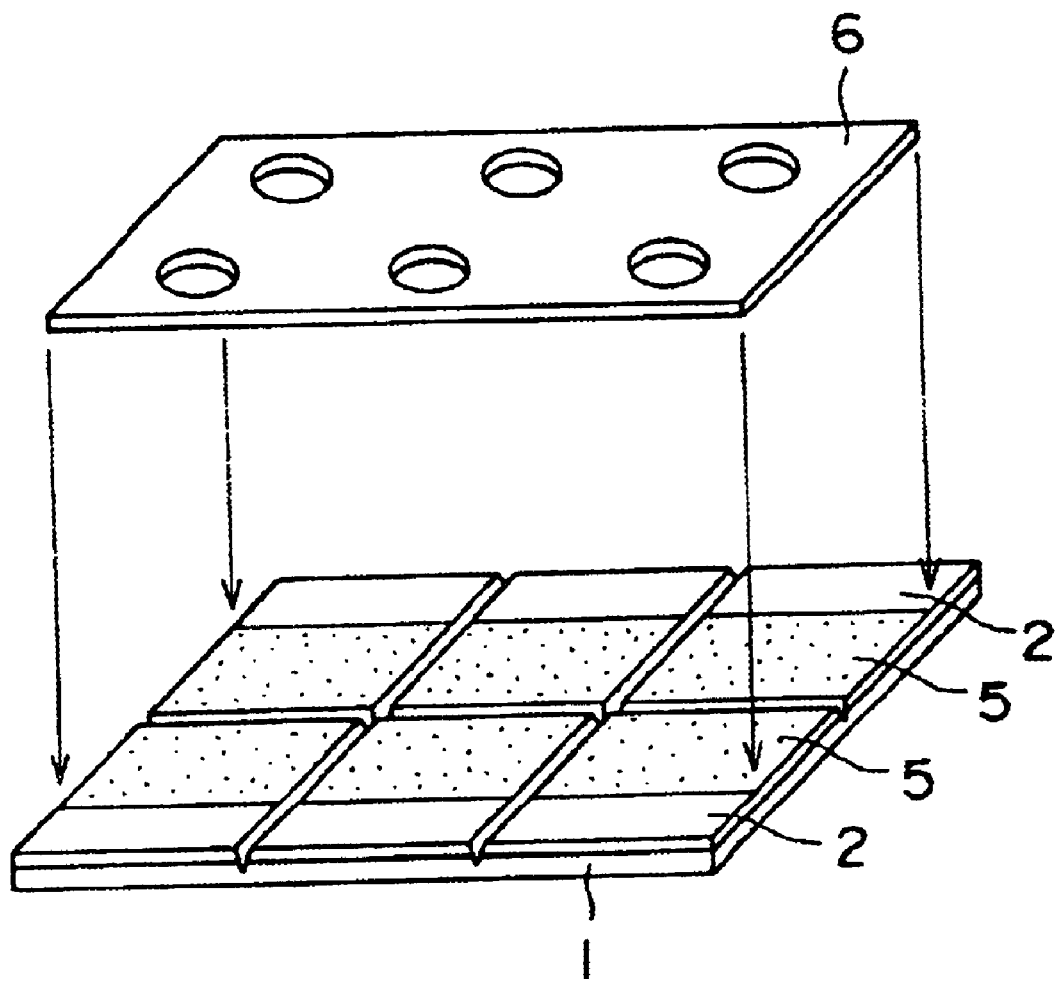
FIG. 2 illustrates a procedure of placing a mask having openings on an electrolytic material layer coated on the electrode layer divided into plural portions in the procedure of FIG. 1.

As is seen in FIG. 2, on the plural electrode layers are coated an electrolytic material layer 5. The electrolytic material generally is a sodium halide or a potassium halide. The halide component generally is the same as that of the silver halide layer.

The polymer films 3 placed on both side areas of the silver metal layer 2 are then peeled off from the silver metal layer 2. The electrolytic material coated on the polymer films 3 are removed simultaneously with the peeling off of the polymer films 3.

In the next step, a mask 6 having openings are placed on the electrolytic material layer 5 for forming spots of ion selective membrane on the electrolytic material layer above each electrode portion, as is illustrated in FIG. 2. The mask can be made of a plastic material film. The openings of the mask can be round, square, or polygon, and have a size less than the size of the each electrode portion. If desired, the mask can be kept on the electrolytic material layer for serving as a non-electroconductive sheet having openings for receiving a sample solution and a reference solution.

Figure 3:
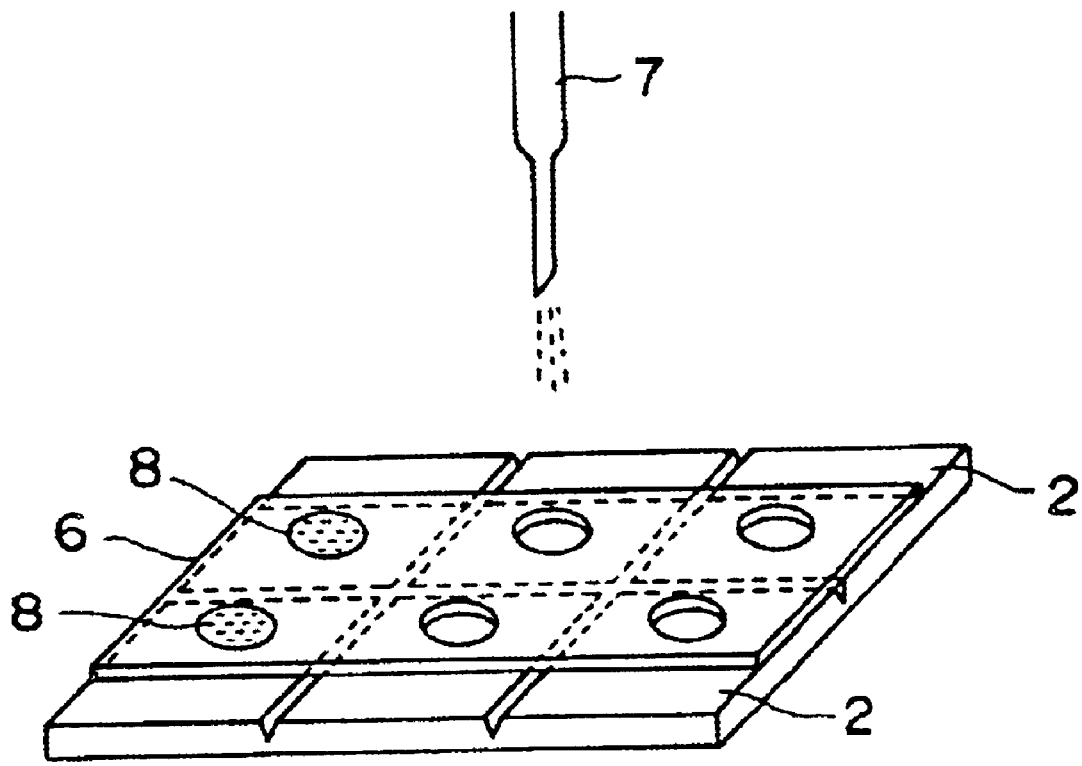
FIG. 3 illustrates a procedure of placing a solution of ion selective membrane material in openings of the mask placed on the electrolytic material layer in the procedure of FIG. 2.

As is illustrated in FIG. 3, in each opening of the mask is spotted a solution of ion selective membrane material using a nozzle 7, so that ion selective membrane in the form of spot 8 are formed independently of each other.

The ion selective membrane material generally comprises an ion carrier and a binder. In the ion selective membrane, the ion carrier is coated generally in an amount of 0.05 to 10 $g/m^2$. The thickness of the ion selective membrane generally is in the range of approx. 3 to 125 $\mu$m, preferably approx. 5 to 50 $\mu$m. The spots of the ion selective membrane generally has a diameter or size of approx. 1 to 10 mm, preferably 2 to 5 mm.

Examples of the ion selective membrane materials are described in the aforementioned U.S. Pat. No. 4,571,293 (corresponding to EP 0 160 997 B1).

The spot of the ion selective membrane can be formed by other methods such as ink jet printing, micro-syringe spotting, screen printing, or gravure printing. In the formation of the ion selective membrane in the form of spots, the use of mask having openings may be omitted. However, the mask can protect the spots of ion selective membrane from physical damage. Accordingly, the use of mask having openings is advantageous.

Figure 4:
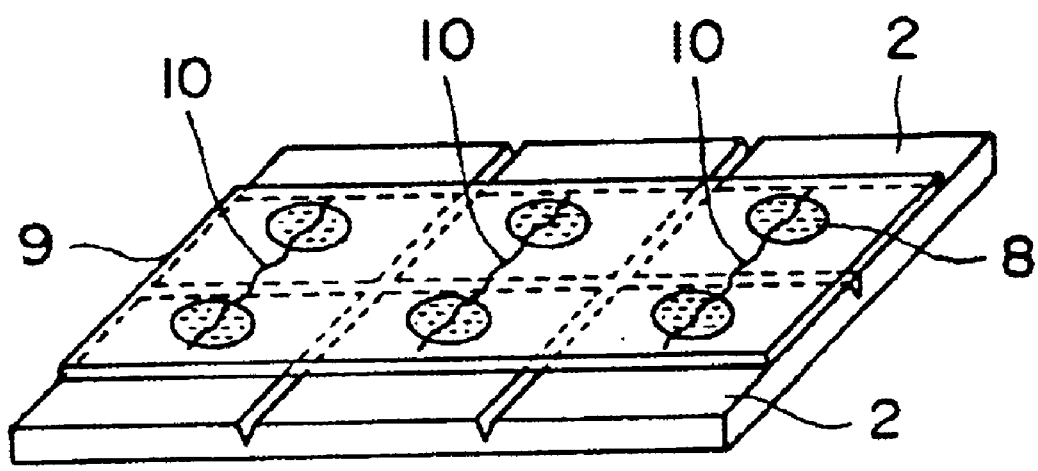
FIG. 4 illustrates a procedure of placing a non-electroconductive sheet having a pair of openings for receiving a sample solution and a reference solution, respectively, each opening being placed above each electrode. The non-electroconductive sheet further has thereon a bridge member for electrically connecting the sample solution received in one opening and the reference solution received in another opening.

As is illustrated in FIG. 4, on the ion selective membrane in the form of spots 8 is placed a non-electroconductive sheet 9 having plural pairs of openings and bridge members 10 under the condition that each opening is placed on each spot 8 of ion selective membrane.

The continuous longitudinal polymer sheet, the electrolytic layer, and the non-electroconductive sheet are then divided at the same time along the slits extending in the traverse direction, to give an ion selective electrode unit.

Figure 5:
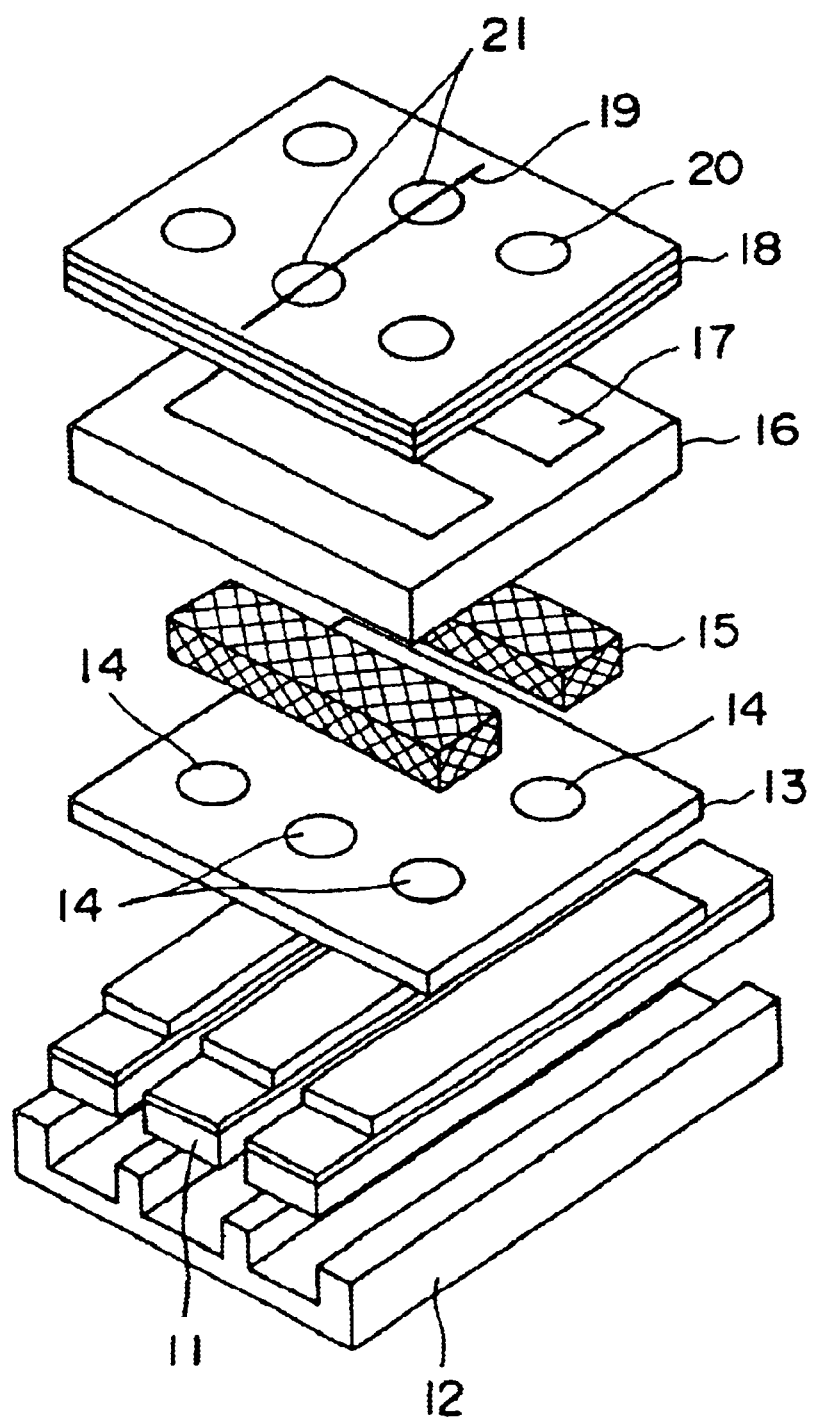
FIG. 5 schematically illustrates a typical structure of an ion selective electrode assembly of the invention comprising plural ion selective electrodes for analyzing plural ionic components simultaneously.
Figure 6:
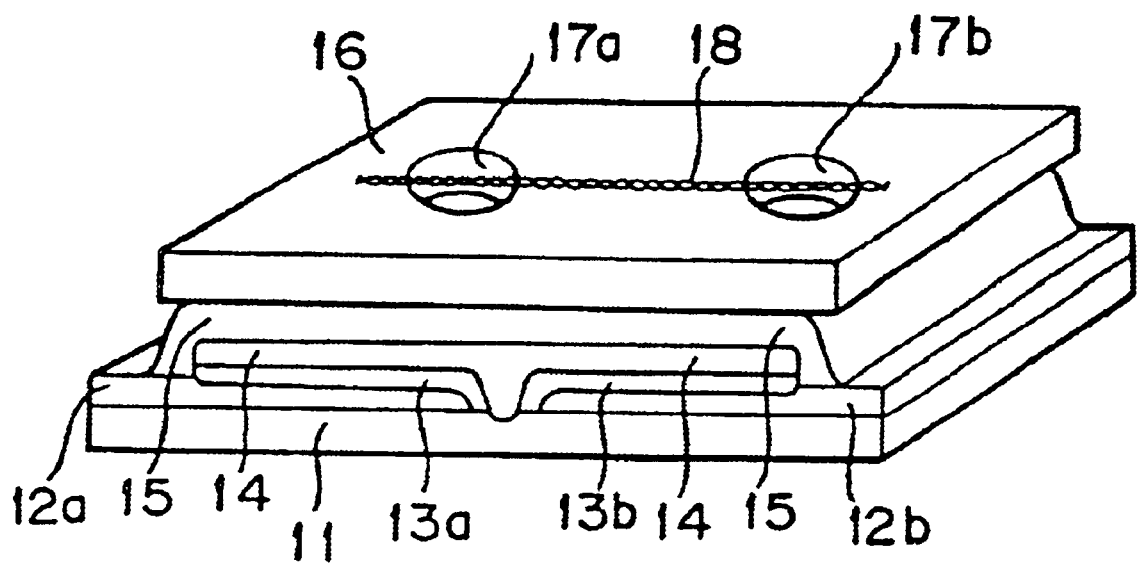
FIG. 6 illustrates a representative structure of a conventional ion selective electrode.

A plurality of ion selective electrode units can be assembled to give an ion selective electrode assembly comprising plural ion selective electrodes of the invention, in which one of plural ion selective electrodes has an ion selective membrane differing from that of other ion selective electrode in chemical composition. A typical structure of the ion selective electrode assembly is illustrated in FIG. 5.

The assembly is composed of ion selective electrode unit of the invention 11, a frame 12 (made of, for instance, high impact polystyrene resin), an intermediate mask sheet 13 having solution-supplying openings 14, solution distributing porous materials (made of, for instance, surgical gauze) 15, a frame 16 having reservoirs 17 for receiving the solution distributing porous materials 15, a solution receiving plate 18 having thereon a bridge member (made of, for instance, polyamide fibers) 19 which are placed on openings 21, one for a sample solution and another for a reference solution. The openings 20 serve as air vents. Details of the structures of ion selective electrode assembly using conventional ion selective electrode units are described in the aforementioned U.S. Pat. No. 4,789,435.

The present invention is further described in the following examples.

EXAMPLE 1

On a longitudinal polyethylene terephthalate film (support, thickness 180 $\mu$m, length 150 m) was coated a silver metal layer (thickness approx. 8,000 angstroms) by continuous vacuum deposition. The film was slitted in the longitudinal direction to give a continuous silver metal-coated strip having a width of 24 mm. On both side areas (width 3 mm) of the silver metal layer was coated with a film-forming a resist resin solution (vinyl chloride-vinyl acetate copolymer in a mixture of toluene and methyl ethyl ketone) and dried to form a coat layer having a thickness of 30 μm.

At the center on the silver metal layer of the strip was provided a groove or scratch (depth 70 μm) extending in the longitudinal direction. A number of grooves are further provided on the silver metal layer in the traverse direction at an interval of 6 mm.

The strip was then placed in an aqueous oxidation-halogenation processing solution containing 60 mM of hydrochloric acid and 12 mM of potassium dichromate for 90 seconds, for performing catalytic oxidation-chlorination processing. The processed strip was recovered, washed with water, and dried to give a strip having on its surface plural Ag/AgCl electrode composites.

A solution of electrolytic material was prepared by dissolving 2.975 g of sodium chloride in 42.5 g of an aqueous organic solvent mixture of 2.5 g of acetone, 20 g of ethanol, and 20 g of water. The solution was then coated on the Ag/AgCl electrode composites and dried to give an electrolytic material layer in an amount of 2.2 g/m$^2$.

The polymer films were peeled off from the silver metal layer. Subsequently, a mask film having six openings arranged in two rows (diameter of opening 2.6 mm, spaces between two adjacent openings 8 mm for traverse direction, 6 mm for longitudinal direction) was placed on the electrolytic material layer in such manner that each opening was positioned in an area surrounded by the grooves. See FIG. 2.

Separately, the following three coating solutions of ion selective membrane materials were prepared:

(1) Composition of sodium ion selective membrane-forming solution

| | |
|---|---|
| Vinyl chloride-vinyl acetate copolymer (VYNS, available from Union Carbide) | 0.9 g |
| Phenyl dicresyl phosphate | 1.2 g |
| Methylmonensin | 0.1 g |
| Sodium tetraphenylborate | 2 mg |
| Methyl ethyl ketone | 4 g |

(2) Composition of potassium ion selective membrane-forming solution

| | |
|---|---|
| VYNS | 0.9 g |
| Dioctyl adipate | 1.2 g |
| Valinomycin | 44 mg |
| Potassium tetrakis-p-chlorophenylborate | 18 mg |
| Methyl ethyl ketone | 5 g |
| 1% SH510 (polysiloxane in methyl ethyl ketone) | 50 mg |

(3) Composition of chloride ion selective membrane-forming solution

| | |
|---|---|
| VYNS | 0.9 g |
| Capricoat | 1.3 g |
| Didodecyl phthalate | 0.05 g |
| Ammonium trioctylpropylchloride | 0.05 g |

Each of the compositions were spotted on each opening of the mask in an amount of 3 μL for each, using a micro-dispenser, to give three sets of a pair of ion selective membranes. The mask was then separated from the electrolytic material layer.

The strip was sequentially cut in the traverse direction to give three ion selective electrode units, respectively, for analysis of Na$^+$, K$^+$ and Cl$^-$.

An ion selective electrode assembly having a structure of FIG. 5 was manufactured using the above-produced three ion selective electrode units.

[Evaluation of Ion Selective Electrodes—1](1) Sample solutions (Fuji Drychem Standard Solutions KE-L, -M, -H, named in terms of concentration, available from Fuji Photo Film Co., Ltd.) and a reference solution (RE, available from Fuji Photo Film Co., Ltd.) were employed for evaluation.

Each of the sample solution and the reference solution was spotted into an opening of the ion selective electrode assembly in an amount of 60 μL per each, and the differential electric potential was measured after keeping the spotted solution at 25° C. for one minute by means of an ion analyzer (Model 901, available from Orion Corporation).

(2) Results of measurement of differential potential

TABLE 1

| | Item of Analysis | KE-L | KE-M | KE-H |
|---|---|---|---|---|
| Na | Measured value (mEq/L) | 99.1 | 139.7 | 179 |
| | CV (%) | 0.65 | 0.34 | 0.41 |
| K | Measured value (mEq/L) | 2.53 | 4.06 | 6.38 |
| | CV (%) | 4.0 | 1.69 | 1.96 |
| Cl | Measured value (mEq/L) | 64.9 | 95.9 | 133.9 |
| | CV (%) | 1.25 | 0.89 | 0.64 |

Remarks: CV means a coefficient of variation

The results set forth in Table 1 are satisfactory, because the CV values are very low. The low CV values mean that the reproducibility of measurement is high.

[Evaluation of Ion Selective Electrodes—2]

(1) Whole blood sample solutions (WB-L, WB-M, WB-H, named in terms of concentration) were employed as sample solution and the same reference solution (RE) was employed for evaluation. The whole blood sample solution was collected in the presence of heparin lithium (anti-coagulating agent). The concentration was adjusted by diluting the sample with a 7% human albumin solution or adding NaCl or KCl.

The evaluation procedures described in the Evaluation of Ion Selective Electrodes—1 were repeated.

(2) Results of measurement of differential potential

TABLE 2

| | Item of Analysis | WB-L | WB-M | WB-H |
|---|---|---|---|---|
| Na | Measured value (mEq/L) | 103 | 144.6 | 163.5 |
| | CV (%) | 0.31 | 0.47 | 0.46 |
| K | Measured value (mEq/L) | 2.62 | 3.74 | 5.75 |
| | CV (%) | 7.6 | 2.02 | 1.32 |

TABLE 2-continued

| | Item of Analysis | WB-L | WB-M | WB-H |
|---|---|---|---|---|
| Cl | Measured value (mEq/L) | 68.9 | 101.7 | 120.2 |
| | CV (%) | 0.93 | 0.66 | 0.62 |

The results set forth in Table 2 are also satisfactory, because the CV values are very low. The low CV values mean that the reproducibility of measurement is high.

What is claimed is:

1. A method of manufacturing an ion selective electrode which comprises the steps of:

preparing a continuos longitudinal polymer sheet having thereon a composite film of a silver metal layer and a silver halide layer, and an electrolytic material layer, in order, in which the composite film is divided into two electrically insulated portions by a slit extending in a longitudinal direction thereof and further into plural electrically insulated units by slits extending in a direction traversing the longitudinal direction;

placing a spot of ion selective membrane material on the electrolytic material layer of the individual electrically insulated unit whereby forming an ion selective membrane on individual electrolytic material layer under the condition that each ion selective membrane is isolated from adjacent ion selective membranes;

placing a non-electroconductive sheet having plural pairs of openings and bridge members under the condition that each opening is placed on each spot of ion selective membrane; and dividing the continuous longitudinal polymer sheet, the electrolytic layer, and the non-electroconductive sheet along the slits extending in the traverse direction.

2. The method of claim 1, wherein the spot of ion selective membrane material is place on the electrolytic material layer by ink jet printing, or micro-syringe spotting.

* * * * *